Feb. 5, 1974 A. M. SHAMMARELLO Plant Pat. 3,465
AZALEA PLANT
Filed Dec. 17, 1971
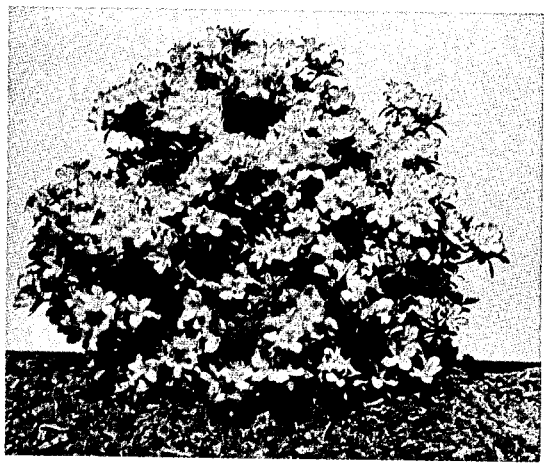

United States Patent Office

Plant Pat. 3,465
Patented Feb. 5, 1974

3,465

AZALEA PLANT

Anthony M. Shammarello, 4590 Monticello Blvd., Cleveland, Ohio 44143

Filed Dec. 17, 1971, Ser. No. 209,481
Int. Cl. A01h *5/00*
U.S. Cl. Plt.—57 1 Claim

The present invention relates to a new and distinct variety of azalea plant of the Kurume type, and is the result of a definite breeding program.

The principal object of this breeding program was to produce a new variety of azelea plant which is dwarf, evergreen and of bushy compact growing character having a hardiness in the Northern part of Ohio similar to that of the Hino-Red parent of Kurume character of growth, and in which the flowers are radiant dark red, having less yellow than Hino-Red, and a darker red than any hardy evergreen azalea grown in Northern Ohio. The object was to create a hardy evergreen with the flower color resembling azalea Wards Ruby.

Seed parent—Hino-Red Plant Pat. No. 2,507, granted May 11, 1965 to Anthony M. Shammarello.

Pollen parent—Wards Ruby.

My new variety has been found to retain its distinctive characteristics through successive asexual reproduction by means of cutting in the vicinity of South Euclid, Ohio.

The hardiness of the plant and flower buds of my new variety is indicated by the fact that they were not adversely affected by a temperature of −12 degrees Fahrenheit during the winter of 1970–1971 in the vicinity of South Euclid, Ohio.

The flowers of my new variety are even larger than those of Hino-Red which in turn were almost twice the size of the Kurume parent of that plant, namely, Hino-Crimson.

The accompanying drawing, forming a part hereof, shows a typical plant of my new variety of azalea, the color of the latter being as nearly true as it is reasonably possible to make the same in a color illustration of this character.

The following is a detailed description of my new variety of azalea plant, color references being to Nickerson Color Fan as published by Munsell Color Company, except where otherwise indicated.

Type: Hardy-evergreen.
Parent: Seed parent—Hino-Red Plant Pat. No. 2,507, granted May 11, 1965 to Anthony M. Shammarello.
Pollen parent: Wards Ruby.
Form of plant: Bushy; compact.

Growing habit: Medium; low branched; from a cutting attained height of about sixteen inches and a width of about twenty-two inches in four years.
Blooming season: About May 20th.
Young shoots: Stems—color 10Y 4/3 moderate olive.
Mature shoots: Color—7.5YR 4/5 moderate brown.
Foliage:
- *Color of young leaves.*—2.5Gy 6/8 strong yellow green.
- *Color of mature leaves.*—5Gy 3/2 grayish olive green.
- *Color of hair on leaf.*—White.
- *Arrangement of leaves.*—In a spiral.
- *Form of leaves.*—Elliptical to oval.
- *Size of leaves.*—1½ inches to 1¾ inches long; ¾ inches to ⅞ inches wide.

Flower:
- *Type.*—Single.
- *Borne.*—Three to four in a cluster.
- *Quantity.*—Abundant.
- *Form.*—Five petals.
- *Size.*—Petal spread 1¾ inches to 2 inches wide.
- *Blotch.*—None.
- *Color.*—Red Group 47B of the Royal Horticultural Society Color Chart.

Reproductive organs:
- *Stamens.*—Six; color 2.5R 4/10 moderate red; about one inch long.
- *Pistil.*—Color 2.5R 4/10 moderate red; length about 1¼ inches.

Leaf texture: Firm; color of reverse side of leaves 2.5Gy 5/5 moderate yellow green; degree of leaf pubescence—moderate.
Flower petals:
- *Texture.*—Firm.
- *Fragrance.*—None.

I claim:

1. A new and distinct variety of azalea plant of the hardy evergreen type, substantially as herein shown and described, characterized particularly as to novelty by the radiant dark red color of its flowers resembling Wards Ruby, by the absence of fading of the flowers when exposed to the sun, by the hardiness of the plant and buds at low temperatures equal to the parent Hino-Red, by flowers slightly larger than the parent plant Hino-Red, and retaining the good qualities of the plant character of Hino-Red.

No references cited.

ROBERT E. BAGWILL, Primary Examiner